United States Patent
Sugahara

(10) Patent No.: US 10,335,103 B2
(45) Date of Patent: Jul. 2, 2019

(54) IMAGE DISPLAY SYSTEM, RADIATION IMAGING SYSTEM, RECORDING MEDIUM STORING IMAGE DISPLAY CONTROL PROGRAM, AND IMAGE DISPLAY CONTROL METHOD

(71) Applicant: FUJIFILM CORPORATION, Minato-ku, Tokyo (JP)

(72) Inventor: Masataka Sugahara, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 406 days.

(21) Appl. No.: 14/663,462

(22) Filed: Mar. 20, 2015

(65) Prior Publication Data

US 2015/0190105 A1 Jul. 9, 2015

Related U.S. Application Data

(63) Continuation of application No. PCT/JP2013/075947, filed on Sep. 25, 2013.

(30) Foreign Application Priority Data

Sep. 28, 2012 (JP) .................... 2012-218256

(51) Int. Cl.
*A61B 6/00* (2006.01)
*A61B 6/03* (2006.01)
(Continued)

(52) U.S. Cl.
CPC ............ *A61B 6/463* (2013.01); *A61B 6/0492* (2013.01); *A61B 6/461* (2013.01); *A61B 6/502* (2013.01);
(Continued)

(58) Field of Classification Search
CPC .... A61B 6/00; A61B 6/02; A61B 6/03; A61B 6/04; A61B 6/0407; A61B 6/0414;
(Continued)

(56) References Cited

U.S. PATENT DOCUMENTS 6,216,029 B1 * 4/2001 Paltieli ................. A61B 8/0833
600/411
2006/0029268 A1 2/2006 Endo et al.
(Continued)

FOREIGN PATENT DOCUMENTS

| JP | 2006-068506 A | 3/2006 | |
| JP | 2010-094397 A | 4/2010 | |
| JP | WO 2013046709 A1 * | 4/2013 | ............. A61B 6/022 |

OTHER PUBLICATIONS

Partial English language translation of the following: Office Action dated Oct. 20, 2015 from the JPO in a Japanese patent application corresponding to the instant patent application.
(Continued)

*Primary Examiner* — Anastasia Midkiff
(74) *Attorney, Agent, or Firm* — SOLARIS Intellectual Property Group, PLLC

(57) ABSTRACT

An image display system, radiation imaging system, image display control program and image display control method, which make the position of an object of interest easier to perceive, are provided. A tomographic image generation section generates a tomographic image DG. A nipple height specification section specifies the height of a nipple P as measured from an imaging plane on the basis of the generated tomographic image DG. An image display control section controls displays at a display, via an interface section, such that an information image IG is displayed together with the generated tomographic image DG. The information image IG indicates the height of the nipple P
(Continued)

and the slice height of the tomographic image DG that is being displayed.

12 Claims, 10 Drawing Sheets

(51) Int. Cl.
    *A61B 6/04*         (2006.01)
    *A61B 6/12*         (2006.01)
    *G06T 7/00*        (2017.01)
    *G06T 7/73*        (2017.01)
    *G06T 11/00*      (2006.01)

(52) U.S. Cl.
    CPC .......... *A61B 6/5294* (2013.01); *G06T 7/0014* (2013.01); *G06T 7/73* (2017.01); *A61B 6/03* (2013.01); *A61B 6/0414* (2013.01); *A61B 6/12* (2013.01); *A61B 2576/02* (2013.01); *G06T 11/008* (2013.01); *G06T 2207/10081* (2013.01); *G06T 2207/30068* (2013.01); *G06T 2207/30096* (2013.01); *G06T 2211/412* (2013.01); *G06T 2211/436* (2013.01)

(58) Field of Classification Search
    CPC ......... A61B 6/0492; A61B 6/46; A61B 6/461; A61B 6/463; A61B 6/48; A61B 6/50; A61B 6/502; A61B 6/52; A61B 6/5211; A61B 6/5223; A61B 6/5294; A61B 2560/00; A61B 2560/02; A61B 2560/06; A61B 2576/00; A61B 2576/02; G06T 7/00; G06T 7/0002; G06T 7/0012; G06T 7/0014; G06T 7/0016; G06T 7/50; G06T 7/55; G06T 7/70; G06T 7/73; G06T 11/00; G06T 11/003; G06T 11/006; G06T 15/00; G06T 15/08; G06T 15/10; G06T 19/00; G06T 19/003; G06T 2207/00; G06T 2207/10; G06T 2207/10072; G06T 2207/10076; G06T 2207/10081; G06T 2207/10112; G06T 2207/10116; G06T 2207/20; G06T 2207/20004; G06T 2207/20036; G06T 2207/30; G06T 2207/30004; G06T 2207/30068; G06T 2207/30096; G06T 2211/00; G06T 2211/40; G06T 2211/412; G06T 2211/424

See application file for complete search history.

(56) References Cited

U.S. PATENT DOCUMENTS

| | | | |
|---|---|---|---|
| 2011/0123087 A1* | 5/2011 | Nie | G06T 7/62 382/132 |
| 2011/0135185 A1 | 6/2011 | Gkanatsios et al. | |
| 2012/0157819 A1* | 6/2012 | Jerebko | A61B 6/5217 600/407 |
| 2014/0213895 A1* | 7/2014 | Kuwabara | A61B 6/022 600/424 |

OTHER PUBLICATIONS

Written Opinion of the ISA issued in International Application No. PCT/JP2013/075947 dated Dec. 3, 2013.

International Search Report issued in International Application No. PCT/JP2013/075947 dated Dec. 3, 2013.

European Extended Search Report dated Apr. 18, 2016 in the corresponding European Patent Application No. 13840971. The EESR is submitted now in order to supplement the understanding of the cited reference which is being disclosed in the instant Information Disclosure Statement.

\* cited by examiner

IMAGE DISPLAY SYSTEM, RADIATION IMAGING SYSTEM, RECORDING MEDIUM STORING IMAGE DISPLAY CONTROL PROGRAM, AND IMAGE DISPLAY CONTROL METHOD

CROSS-REFERENCE TO RELATED APPLICATION

This application is a continuation application of International Application No. PCT/JP2013/075947, filed Sep. 25, 2013, the disclosure of which is incorporated herein by reference in its entirety. Further, this application claims priority from Japanese Patent Application No. 2012-218256, filed Sep. 28, 2012, the disclosure of which is incorporated herein by reference in its entirety.

FIELD

The present disclosure relates to an image display system, a radiation imaging system, a recording medium storing an image display control program, and an image display control method.

BACKGROUND

For purposes of clinical diagnostics, radiation is irradiated at an imaging subject examinee who is a patient and a radiation image is captured by a radiation imaging device. As this radiation imaging device, a radiation imaging device that captures radiation images of the breasts of examinees is known, and is referred to as a "mammography device".

Tomosynthesis imaging is known as an imaging method. In tomosynthesis imaging, radiation is irradiated at a breast from plural directions and radiation images thereof are captured, and tomographic images are generated on the basis of the captured radiation images.

Tomosynthesis imaging commonly generates a plural number of tomographic images. Accordingly, there are technologies that display to a user, such as a doctor or the like who is interpreting the tomographic images for diagnosis or the like, which position (slice) a tomographic image that is being interpreted corresponds with.

For example, Japanese Patent Application Laid-Open (JP-A) No. 2010-94397 recites a technology that, when mammogram tomographic image data obtained by tomosynthesis imaging is being displayed, employs a schematic thumbnail image that shows the breast from a side face thereof and displays a bar showing which slice is currently being displayed.

SUMMARY

An aspect of the present disclosure is an image display system including: a tomographic image generation unit that irradiates radiation, from a radiation irradiation unit disposed to oppose a radiation image detector, at a breast on the radiation image detector from different angles, acquires a plurality of radiation images captured by the radiation image detector at the respective angles from the radiation image detector and, on the basis of the acquired plurality of radiation images, generates a tomographic image that is reconstructed by reference to a detection plane of the radiation image detector; a height specification unit that specifies a height of a nipple of the breast by reference to the detection plane; and a display control unit that controls to cause a display unit to display the tomographic image together with information relating to the nipple height specified by the height specification unit.

DESCRIPTION OF EMBODIMENTS

Herebelow, an exemplary embodiment of the present disclosure is described in detail with reference to the attached drawings. Note that the present exemplary embodiment does not limit the present disclosure.

Figure 1:
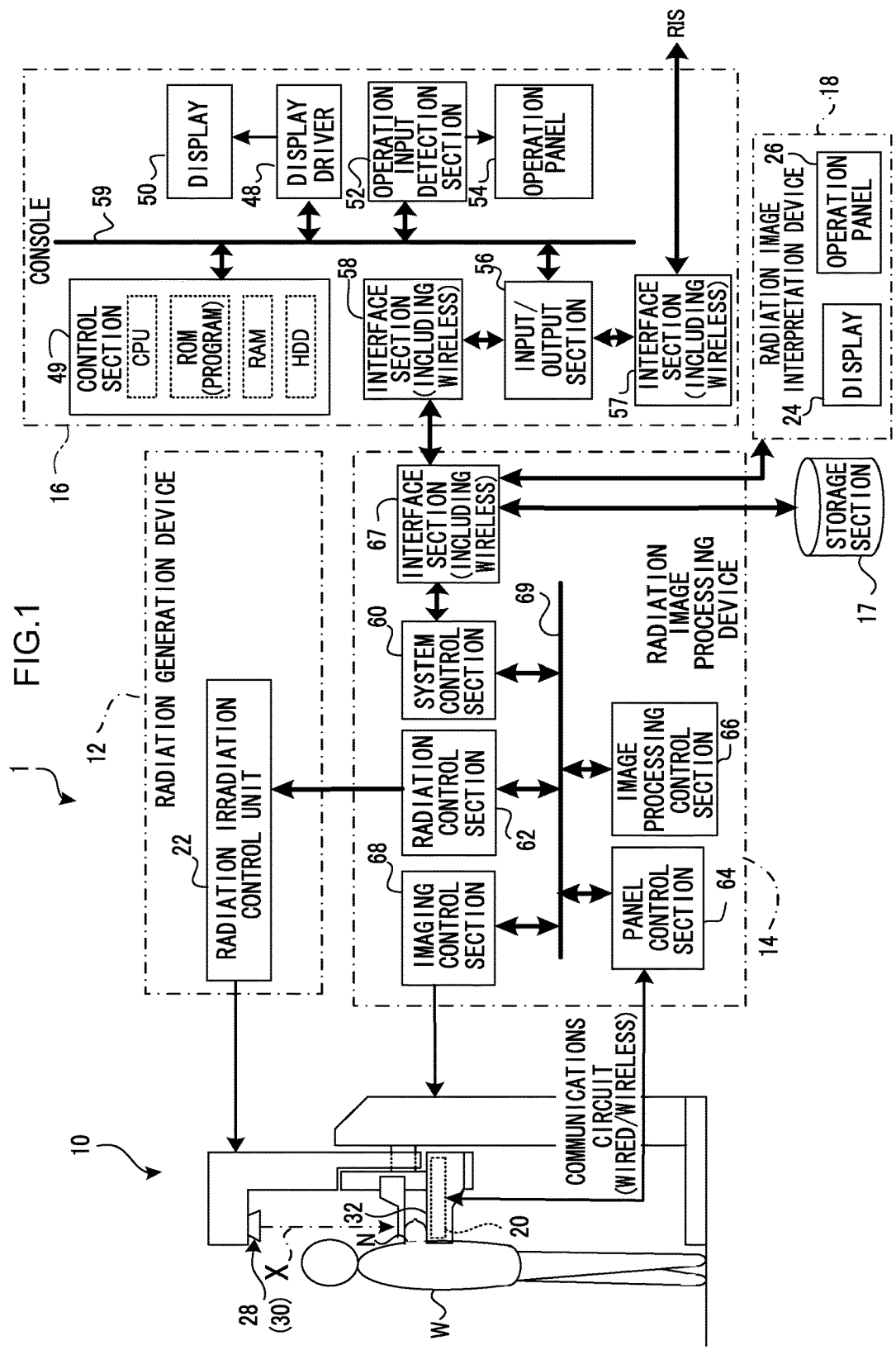
FIG. 1 is a schematic structural diagram showing the schematics of the overall structure of an example of a radiation imaging system in accordance with a present exemplary embodiment.

First, the overall schematic structure of a radiation imaging system according to the present exemplary embodiment is described. FIG. 1 shows a schematic structural diagram of an example of the overall structure of the radiation imaging system according to the present exemplary embodiment.

The radiation imaging system 1 according to the present exemplary embodiment includes functions for capturing radiation images in response to operations by doctors, radiographers and the like on the basis of instructions (imaging menu selections) inputted from an external system (for example, a radiology information system (RIS)) via a console 16. In the present exemplary embodiment, a doctor or the like or a radiographer, an operator, a person performing an observation, examination, diagnosis or the like of an object of interest such as a calcinosis, a tumor, a mammary gland or the like with captured radiation images, or the like is referred to as "the user". A tissue or a diseased portion such as a calcinosis, a tumor or the like that is the target of the user's observation, examination, diagnosis or the like is referred to as "the object of interest". The object of interest may be something other than human tissue.

The radiation imaging system 1 according to the present exemplary embodiment also includes functions that enable doctors, radiographers and the like to interpret radiation images, by displaying the radiation images at a display 50 of the console 16 or at a radiation image interpretation device 18 or the like.

The radiation imaging system 1 according to the present exemplary embodiment is equipped with a radiation imaging device 10, a radiation generation device 12, a radiation image processing device 14, the console 16, a storage section 17, the radiation image interpretation device 18 and an electronic cassette 20.

The radiation generation device 12 includes a radiation irradiation control unit 22. The radiation irradiation control unit 22 includes a function for causing an irradiation of radiation X from a radiation irradiation section 28, at an imaging target region of an imaging subject W (a breast N) on an imaging table 32, in accordance with control by a radiation control section 62 of the radiation image processing device 14.

Radiation X that passes through the imaging subject W is irradiated onto the electronic cassette 20, which is retained inside the imaging table 32. The electronic cassette 20 includes functions for generating electric charges in accordance with doses of the radiation X passing through the imaging subject W, generating image information representing a radiation image on the basis of the generated charge amounts, and outputting the image information.

In the present exemplary embodiment, the image information representing a radiation image that is outputted by the electronic cassette 20 is inputted to the console 16 via the radiation image processing device 14. The console 16 according to the present exemplary embodiment includes functions for controlling the radiation imaging device 10, the radiation generation device 12 and the electronic cassette 20, using imaging menu selections and various other kinds of information acquired from the external system (the RIS) or the like via a wireless network (a local area network (LAN)) or the like. The console 16 according to the present exemplary embodiment includes functions for exchanging various kinds of information, including image information of radiation images, with the radiation image processing device 14.

The console 16 according to the present exemplary embodiment is a server computer. The console 16 includes a control section 49, a display driver 48, the display 50, an operation input detection section 52, an operation panel 54, an input/output section 56, an interface section 57 and an interface section 58. The control section 49, the display driver 48, the operation input detection section 52 and the input/output section 56 are connected to be able to transfer information and the like to one another via a bus 59, which is a system bus, a control bus or the like.

The control section 49 includes functions for controlling overall operations of the console 16, and is provided with a central processing unit (CPU), read-only memory (ROM), random access memory (RAM) and a hard disk drive (HDD). The CPU includes functions for controlling overall operations of the console 16. Various programs, including a control program to be used at the CPU, and suchlike are pre-memorized in the ROM. The RAM includes functions for temporarily storing various kinds of data. The HDD includes functions for storing and retaining various kinds of data.

The display driver 48 includes functions for controlling the display of various kinds of information at the display 50. The display 50 according to the present exemplary embodiment includes functions for displaying imaging menu items, radiation images, tomographic images and the like. The operation input detection section 52 includes functions for detecting operation states of the operation panel 54. The operation panel 54 is for users to input operation instructions in relation to the imaging of radiation images. The operation panel 54 according to the present exemplary embodiment includes, for example, a touch panel, a touch pen, plural buttons and a mouse, or the like. In a case in which the operation panel 54 is a touch panel, it may be the same component as the display 50.

The input/output section 56 and the interface section 58 include functions for exchanging various kinds of information and image information and the like with the radiation imaging device 10, the radiation generation device 12 and the electronic cassette 20 by wireless communications via the radiation image processing device 14. The interface section 57 includes functions for exchanging various kinds of information with the RIS.

The radiation image processing device 14 according to the present exemplary embodiment includes a system control section 60, the radiation control section 62, a panel control section 64, an image processing control section 66, an interface section 67 and an imaging control section 68.

The system control section 60 includes functions for overall control of the radiation image processing device 14 and functions for controlling the radiation imaging system 1. The radiation control section 62 includes functions for controlling the radiation irradiation control unit 22 of the radiation generation device 12 in accordance with commands from the console 16 and the like. The panel control section 64 includes functions for controlling the electronic cassette 20 in accordance with commands from the console 16 and the like. The image processing control section 66 includes functions for applying various kinds of image processing to radiation images. The imaging control section 68 includes functions for controlling the radiation imaging device 10 in accordance with commands from the console 16 and the like. The system control section 60, the radiation control section 62, the panel control section 64, the image processing control section 66 and the imaging control section 68 are connected to be capable of transferring information and the like to one another via a bus 69, which is a system bus, a control bus or the like.

The storage section 17 according to the present exemplary embodiment includes functions for memorizing captured radiation images and information relating to the radiation images. The storage section 17 may be, for example, an HDD or the like.

The radiation image interpretation device 18 according to the present exemplary embodiment is a device that includes functions for interpretation of the captured radiation images by the user. The radiation image interpretation device 18 is not particularly limited but may be a "radiographic interpretation viewer", a console, a tablet terminal or the like. The radiation image interpretation device 18 according to the present exemplary embodiment is a personal computer. The radiation image interpretation device 18, similarly to the console 16 and the radiation image processing device 14, includes a CPU, ROM, RAM, an HDD, a display driver, a display 24, an operation input detection section, an operation panel 26, an input/output section, and an interface section. In FIG. 1, to avoid complexity in the drawing, only the display 24 and the operation panel 26 are shown of these structures; the other structures are not shown.

Figure 2:
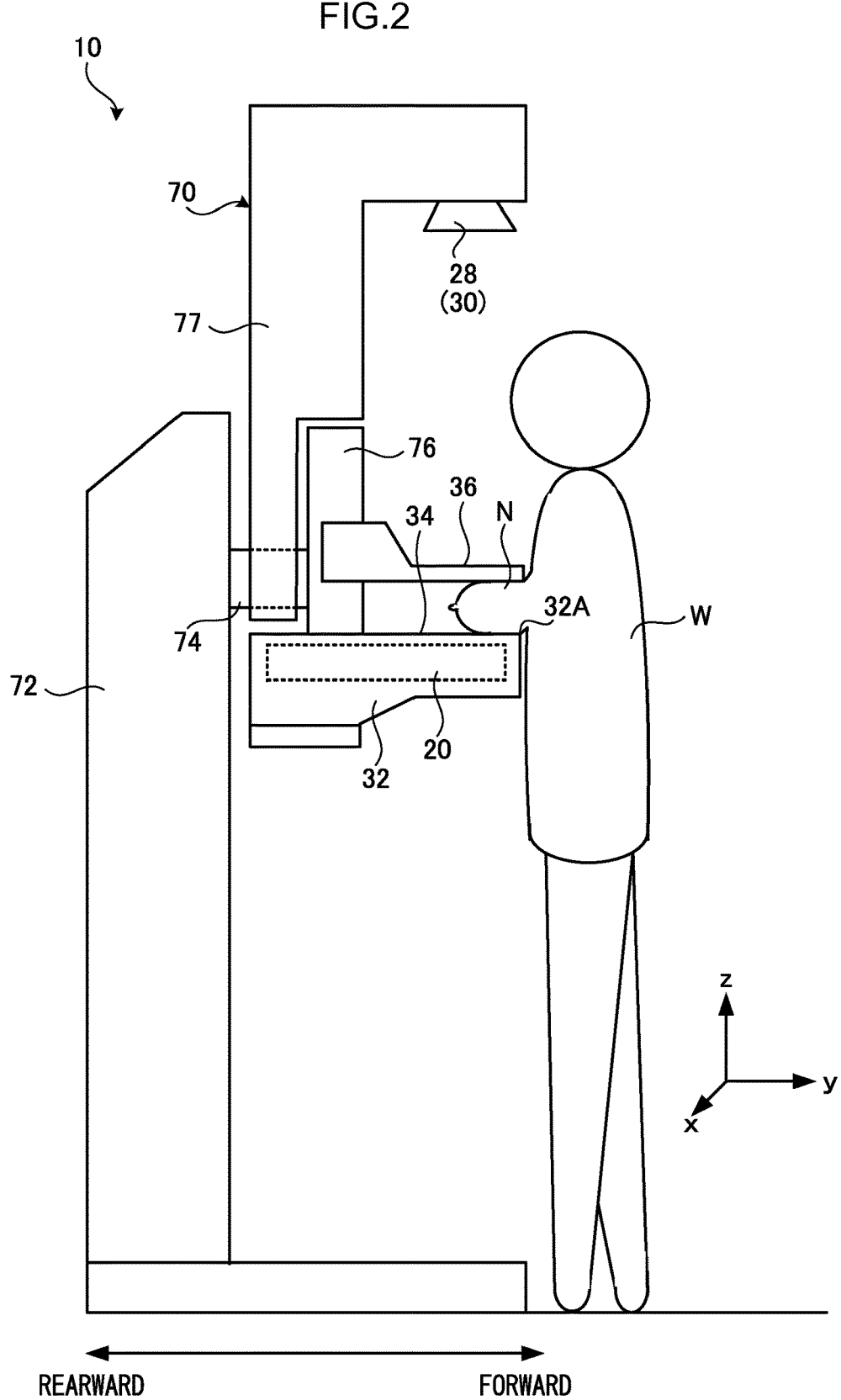
FIG. 2 is a schematic structural diagram showing an example of the structure of a radiation imaging device in accordance with the present exemplary embodiment.
Figure 3:
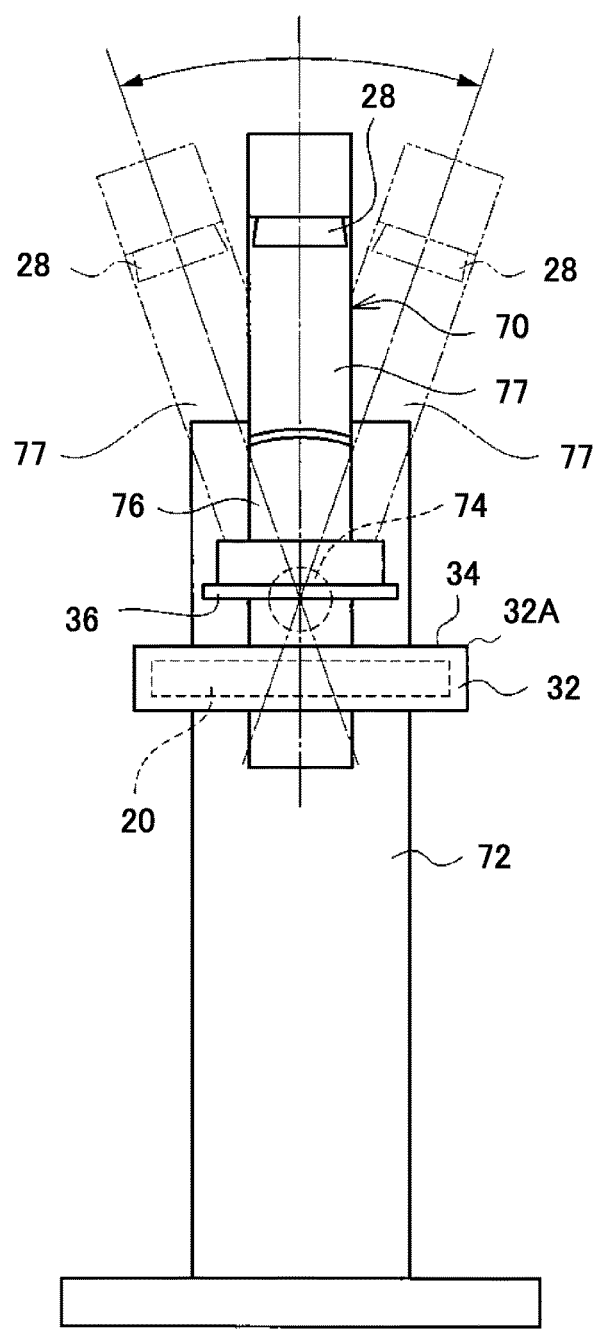
FIG. 3 is a structural diagram showing an example of the structure of the radiation imaging device in accordance with the present exemplary embodiment at times of imaging.
Figure 4:
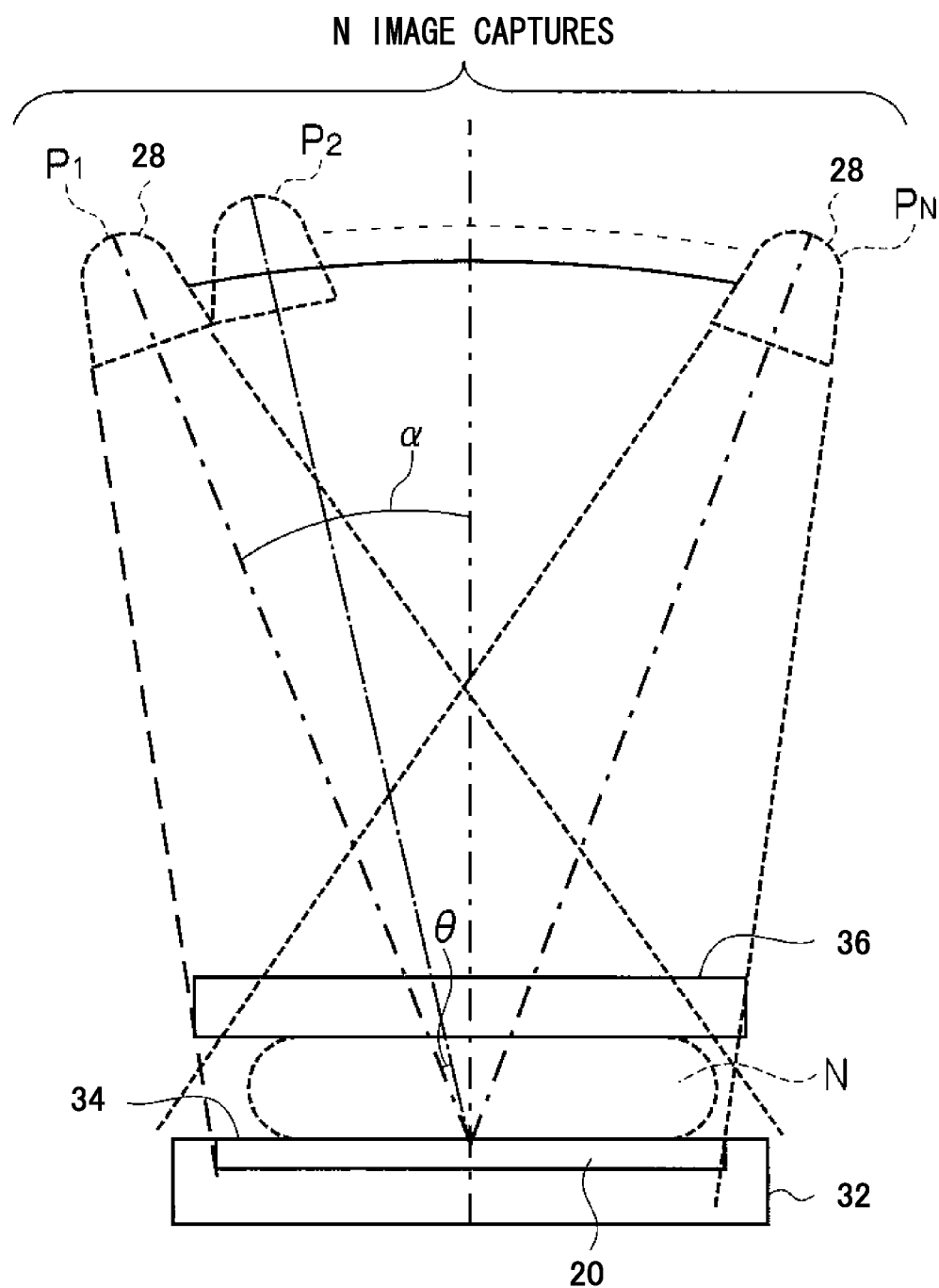
FIG. 4 is a descriptive diagram for describing the radiation imaging device in accordance with the present exemplary embodiment at times of imaging

Now, structures of the radiation imaging device 10 according to the present exemplary embodiment are described in detail. FIG. 2 shows a schematic structural diagram of an example of the structure of the radiation imaging device 10 according to the present exemplary embodiment. FIG. 3 shows a structural diagram of an example of the structure of the radiation imaging device 10 according to the present exemplary embodiment at times of imaging. FIG. 4 is a descriptive diagram for describing the radiation imaging device 10 according to the present exemplary embodiment at times of imaging.

As shown in FIG. 2 to FIG. 4, the radiation imaging device 10 according to the present exemplary embodiment is a device that images the breast N of the imaging subject W with radiation (for example, X-rays) when the imaging subject W is in a standing posture, and is referred to as, for example, a "mammography device". Hereinafter, a side of the radiation imaging device 10 that is closer to the imaging subject W when the imaging subject W is facing the radiation imaging device 10 during imaging is referred to as the device forward side of the radiation imaging device 10, and the far side away from the imaging subject W when the imaging subject W is facing the radiation imaging device 10 is referred to as the device rearward side of the radiation imaging device 10. A left-and-right direction of the imaging subject W when the imaging subject W is facing the radiation imaging device 10 is described as the device left-and-right direction of the radiation imaging device 10 (see the arrows in FIG. 2 to FIG. 4).

The radiation imaging device 10 may also be a device that images the breast N of the imaging subject W when the imaging subject W is in a seated posture, sitting on a chair (which may be a wheelchair) or the like. It is sufficient for the radiation imaging device 10 to be a device that may separately image the left and right breasts N of the imaging subject W in a state in which at least the upper half of the imaging subject W is in an upright posture.

As shown in FIG. 2, the radiation imaging device 10 is provided with a measurement portion 70 and a pedestal portion 72. The measurement portion 70 is provided at the vehicle forward side in a substantial "C" shape in side view. The pedestal portion 72 supports the measurement portion 70 from the vehicle rearward side thereof.

The measurement portion 70 is provided with the imaging table 32, at which a flat plane-shaped imaging surface 34 is formed, a compression plate 36, and a support portion 76. The imaging surface 34 abuts against the breast N of the imaging subject W in the standing posture. The compression plate 36 compresses the breast N against the imaging surface 34 of the imaging table 32. The support portion 76 supports the imaging table 32 and the compression plate 36.

The measurement portion 70 is provided with the radiation irradiation section 28 and a support portion 77. The measurement portion 70 is provided with a radiation source 30, which is a vacuum tube or the like, and irradiates radiation for scanning from the radiation source 30 toward the imaging surface 34. The support portion 77 is set apart from the support portion 76 and supports the radiation irradiation section 28.

The measurement portion 70 is provided with a turning shaft 74, which is turnably supported at the pedestal portion 72. The turning shaft 74 is fixed to the support portion 77. Thus, the turning shaft 74 and the support portion 77 turn integrally.

The support portion 76 is made switchable between a state in which the turning shaft 74 is joined to the support portion 76 and turns integrally therewith, and a state in which the turning shaft 74 is separated from the support portion 76 and turns freely. Specifically, respective gears are provided at the turning shaft 74 and the support portion 76, and these gears are switched between a meshed state with one another and a non-meshed state. Various mechanical elements may be employed for switching between the transmission or non-transmission of rotary force to the turning shaft 74.

The support portion 76 supports the imaging table 32 and the radiation irradiation section 28 such that the imaging surface 34 and the radiation irradiation section 28 are a predetermined distance apart, and the support portion 76 retains the compression plate 36 to be slidable such that a distance between the compression plate 36 and the imaging surface 34 is alterable.

The imaging surface 34 against which the breast N abuts is formed of, for example, carbon, with a view to radiation transmissivity and strength. Radiation that has passed through the breast N and the imaging surface 34 is irradiated to the interior of the imaging table 32. The electronic cassette 20 that detects the radiation is disposed in the interior of the imaging table 32. Radiation detected by the electronic cassette 20 is visualized to generate a radiation image. The electronic cassette 20 receives radiation carrying image information and records the image information, and outputs the recorded image information. The electronic cassette 20 is provided with a radiation detector that detects the image information in the form of electric charges in respective pixels that are generated in response to doses of irradiated radiation. The electronic cassette 20 may be, for example, a flat panel detector (FPD) in which a radiation sensitive layer is disposed, and that converts the radiation to digital data and outputs the digital data.

The radiation imaging device 10 according to the present exemplary embodiment is a device that may perform imaging, at least of the breast N that is an imaging subject, from plural directions. FIG. 3 and FIG. 4 show attitudes of the radiation imaging device 10 at respective times of imaging and positions of the radiation irradiation section 28 at these times of imaging. As shown in FIG. 3 and FIG. 4, this imaging is imaging in which the support portion 77 is tilted.

In the radiation imaging device 10, as shown in FIG. 4, in a case of imaging of the breast N from plural directions (tomosynthesis imaging), the turning shaft 74 turns freely relative to the support portion 76. Thus, the radiation irradiation section 28 alone is turned through a circular arc by the support portion 77 turning, without the imaging table 32 and the compression plate 36 being moved. In the present exemplary embodiment, as shown in FIG. 4, the imaging position is moved in units of a predetermined angle θ from an angle α, and imaging is performed with the position of the radiation irradiation section 28 being at N positions, P1 to PN.

The radiation imaging device 10 according to the present exemplary embodiment is a device that may carry out both cranio-caudal (CC; the head-to-foot direction) imaging and mediolateral-oblique (MLO; a diagonal in-to-out direction) imaging of the breast N. At a time of CC imaging, the attitude of the support portion 76 is adjusted to a state in which the imaging surface 34 is facing upward, and the attitude of the support portion 76 is adjusted to a state in which the radiation irradiation section 28 is disposed above the imaging surface 34. Hence, in the radiation imaging device 10, radiation is irradiated from the radiation irradiation section 28 to the breast N, in a direction from the head side toward the feet side of the imaging subject W in the standing state, and the CC imaging is implemented. At a time of MLO imaging, generally, the attitude of the support portion 76 is adjusted to a state in which the imaging surface 34 is turned at least 45° but less than 90° from the state at the time of CC imaging, and a sidewall corner portion 32A at the device forward side of the imaging table 32 is positioned so as to fit into an armpit of the imaging subject W. Hence, in the radiation imaging device 10, radiation is irradiated from the radiation irradiation section 28 to the breast N, in a direction from an axial central side of the torso of the imaging subject W toward the outer side, and the MLO imaging is implemented.

Figure 5:
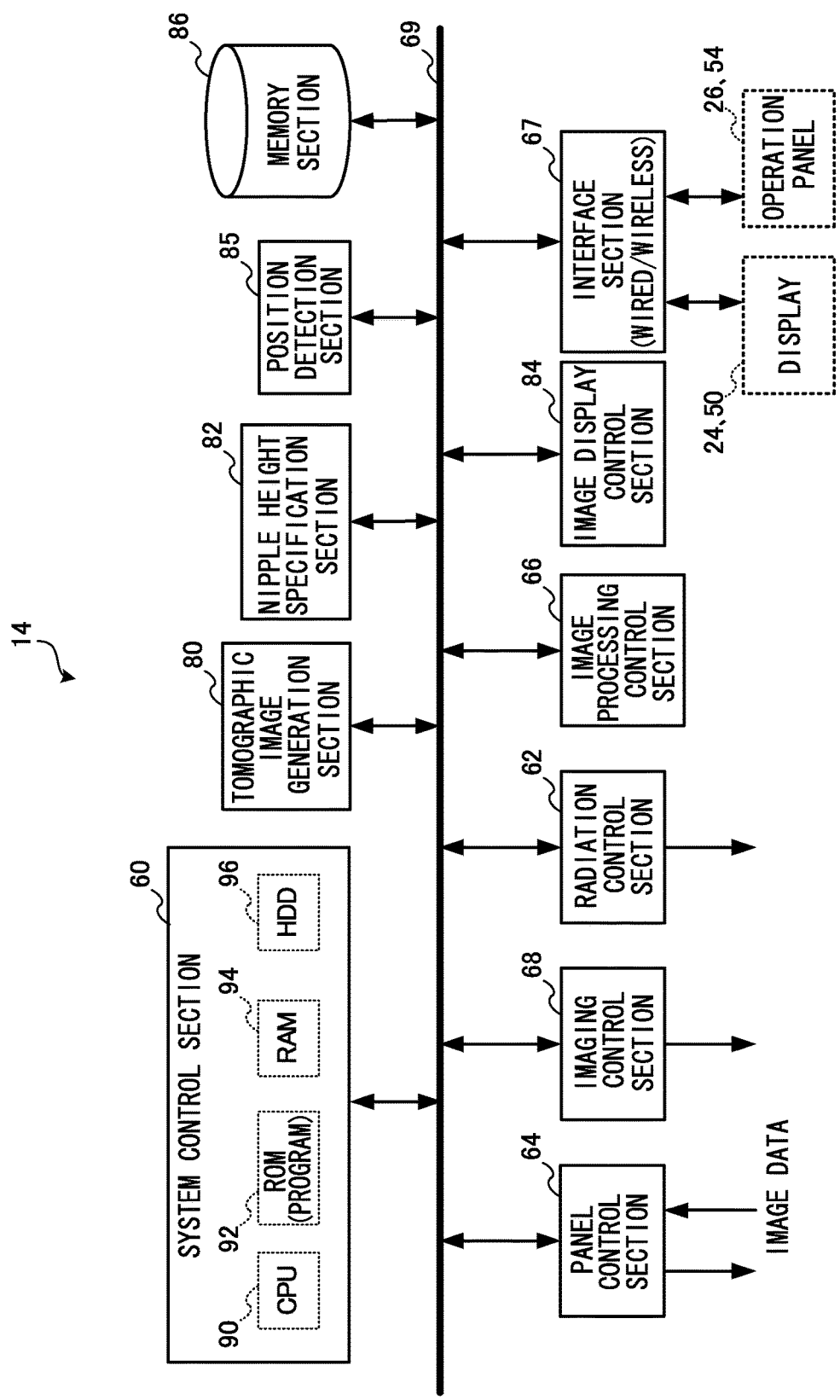
FIG. 5 is a block diagram showing an example of the structure of a radiation image processing device in accordance with the present exemplary embodiment, focusing on an image display control processing function.

Now, a function that implements image display control processing in the radiation image processing device 14 according to the present exemplary embodiment is described. FIG. 5 shows a block diagram of an example of the structure of the radiation image processing device 14, focusing on the image display control processing function.

The radiation image processing device 14 is provided with the system control section 60, the radiation control section 62, the panel control section 64, the image processing control section 66, the interface section 67, the imaging control section 68, a tomographic image generation section 80, a nipple height specification section 82, an image display control section 84, a position detection section 85 and a memory section 86. These are connected to be capable of exchanging information and the like with one another via the bus 69, which is a control bus and data bus or the like.

The system control section 60 includes a function that controls operations of the radiation image processing device 14 as a whole. The system control section 60 includes a CPU 90, a ROM 92, a RAM 94 and an HDD 96. Specifically, the CPU 90 controls the radiation image processing device 14 as a whole by executing a program stored in the ROM 92. The program is stored in the ROM 92 in the present exemplary embodiment, but the program may be memorized on a recording medium such as a CD-ROM, a removable disk or the like and installed in the ROM 92 or the like from the recording medium. The program may also be installed in the ROM 92 or the like from external equipment via a communications circuit such as the Internet or the like. The RAM 94 reserves regions for operations when the CPU 90 is executing the program. The HDD 96 memorizes and stores various kinds of data.

When the radiation control section 62 receives an irradiation command from the console 16 or the like via the interface section 67, the radiation control section 62 irradiates radiation at the imaging surface 34 from the radiation source 30 provided at the radiation irradiation section 28, in accordance with imaging menu selections specified in accordance with designated exposure conditions. Exposure conditions that are received via the interface section 67 include a tube voltage, a tube current, an irradiation duration, attitude information and so forth. The attitude information includes, in a case in which the breast N is being imaged from plural directions, information representing imaging positions (imaging attitudes and angles) or the like.

The exposure conditions, attitude information and the like may be specified by the user at the console 16 or the like, may be obtained from another control device (the RIS) or the like, and may be memorized in the memory section 86 or the like in advance.

When specifications of the various kinds of information have been received, the radiation control section 62 causes radiation X to be irradiated at an imaging region (the breast N) of the imaging subject W from the radiation irradiation section 28 in accordance with imaging menu selections based on the specified various kinds of information, implementing the imaging of a radiation image. In a case of imaging from plural directions, the imaging control section 68 adjusts the attitude of the support portion 76 to the state in which the imaging surface 34 is facing upward and adjusts the attitude of the support portion 77 to the state in which the radiation irradiation section 28 is disposed above the imaging surface 34. In a case of tomosynthesis imaging, as shown in FIG. 4, the support portion 77 is turned and the radiation irradiation section 28 is moved in units of the angle θ from the angle α through the circular arc, and the imaging control section 68 and the radiation control section 62 cause the radiation X to be irradiated at the imaging surface 34 from the radiation source 30 provided at the radiation irradiation section 28 separately at the different angles, in accordance with the imaging conditions. The panel control section 64 drives the electronic cassette 20 in accordance with imaging menu selections. When the radiation X has been irradiated, the electronic cassette 20 outputs image information representing a radiation image to the radiation image processing device 14 via the panel control section 64. In the present exemplary embodiment, the electronic cassette 20 receives irradiations of radiation that has passed through the breast N and obtains image information representing radiation images of N frames.

The tomographic image generation section 80 includes a function that reconstructs tomographic images from the plural radiation images obtained by tomosynthesis imaging, generating tomographic images that are parallel to the imaging surface 34. In the present exemplary embodiment, the term "parallel" includes the meaning "substantially parallel".

The tomographic image generation section 80 generates the tomographic images from the plural radiation images captured at the positions P1, P2, P3, . . . , PN. A position at which an object of interest appears in the radiation images differs depending on the imaging angle at which the radiation source 30 irradiates the radiation from each position. Therefore, the tomographic image generation section 80 acquires the imaging conditions when the radiation images were imaged from the radiation imaging device 10. On the basis of the imaging angles included in the imaging conditions, the tomographic image generation section 80 calculates movement amounts of the object of interest between the plural radiation images, and reconstructs the tomographic images in accordance with a publicly known reconstruction method.

The memory section 86 is for memorizing various kinds of information, and may be a "large-volume" hard disc or the like. In the present exemplary embodiment, the memory section 86 temporarily stores the radiation images acquired from the radiation imaging device 10, the tomographic images generated by the tomographic image generation section 80, and the like.

The nipple height specification section 82 includes a function that specifies a height of a nipple of the breast N at the time of imaging, by reference to the imaging surface 34 (hereinafter, this is simply referred to as "the nipple height"). In the present exemplary embodiment, the nipple height is specified on the basis of tomographic images that include images of the nipple, extracted or designated from the plural tomographic images generated by the tomographic image generation section 80.

The position detection section 85 includes a function that, in a case in which at least one object of interest or region is designated by a user in the tomographic image obtained by one of CC imaging and MLO imaging, detects a position that corresponds to the designated position in a tomographic image obtained by the other kind of imaging.

The image display control section 84 includes a function that controls the display of various images at the display 50 of the console 16 and the display 24 of the radiation image interpretation device 18, or the like, via the interface section 67. The image display control section 84 according to the present exemplary embodiment controls such that a tomographic image generated by the tomographic image generation section 80 is displayed together with information relating to the nipple height specified by the nipple height specification section 82 and information relating to a slice height of the tomographic image.

Now, operations of the radiation imaging system 1 according to the present exemplary embodiment are described with reference to the attached drawings.

First, capture of a radiation image with the radiation imaging device 10 according to the present exemplary embodiment is described. In a case in which a radiation image is being captured, the radiation imaging device 10 executes the imaging in accordance with imaging menu selections.

In a case in which an imaging command for CC imaging is inputted, the radiation imaging device 10 adjusts the attitude of the support portion 76 to the state in which the imaging surface 34 is facing upward and adjusts the attitude of the support portion 77 to the state in which the radiation irradiation section 28 is disposed above the imaging surface 34. In a case in which MLO imaging is commanded, the radiation imaging device 10 adjusts the attitude of the support portion 76 to a state in which the imaging table 32 is turned to a predetermined angle and the imaging surface 34 is tilted.

The imaging subject W abuts the breast N against the imaging surface 34 of the radiation imaging device 10. When an operation command for starting compression is given by the user in this state, the radiation imaging device 10 moves the compression plate 36 toward the imaging surface 34.

If an imaging command for tomosynthesis imaging, in which the breast N is imaged from plural directions, is inputted in this state, the radiation imaging device 10 according to the present exemplary embodiment turns the support portion 77 alone and moves the radiation irradiation section 28 through the circular arc. Thus, as shown in FIG. 4, the imaging position is moved from the angle α in units of the predetermined angle θ, and irradiations of radiation in accordance with respective imaging conditions are performed at N positions, P1 to PN, of the radiation irradiation section 28. The separate irradiations of radiation from the radiation irradiation section 28 respectively reach the electronic cassette 20 after passing through the breast N.

When the radiation is irradiated, the electronic cassette 20 outputs respective image information representing the irradiated radiation images to the panel control section 64. In a case in which, as described above, the irradiations of radiation are performed at the N positions of the radiation irradiation section 28, P1 to PN, the image information of N radiation images is outputted to the panel control section 64.

The radiation image processing device 14 carries out image display control processing to cause a tomographic image reconstructed from the N radiation images according to tomosynthesis imaging, which are inputted from the radiation imaging device 10, and information relating to the nipple height to be displayed at the display 50 of the console 16 and the display 24 of the radiation image interpretation device 18 or the like.

Figure 6:
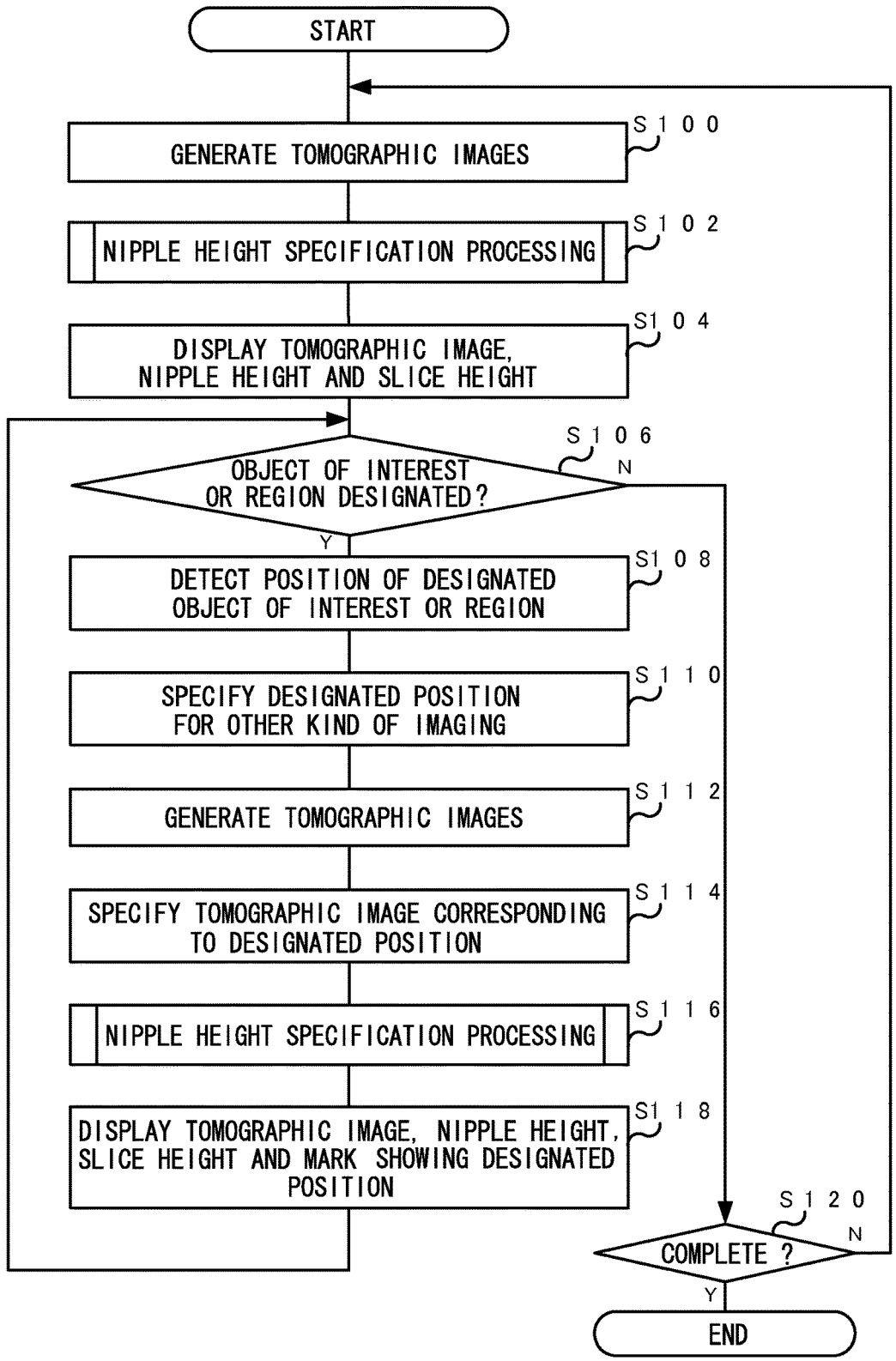
FIG. 6 is a flowchart showing an example of the flow of image display control processing that is executed by the radiation image processing device in accordance with the present exemplary embodiment.

Now, this image display control processing is described in detail. FIG. 6 shows a flowchart of an example of the flow of the image display control processing that is executed by the radiation image processing device 14 according to the present exemplary embodiment.

In step S100, tomographic images are generated by the tomographic image generation section 80. Image information of the radiation images obtained from the electronic cassette 20 via the panel control section 64 is temporarily memorized in the memory section 86.

As mentioned above, the tomographic image generation section 80 reconstructs tomographic images with a predetermined slice thickness in accordance with a publicly known reconstruction method. The plural tomographic images that are generated are temporarily memorized in the memory section 86. In the present exemplary embodiment, the height of a tomographic image from the imaging surface 34 is referred to as "the slice thickness".

Figure 7:
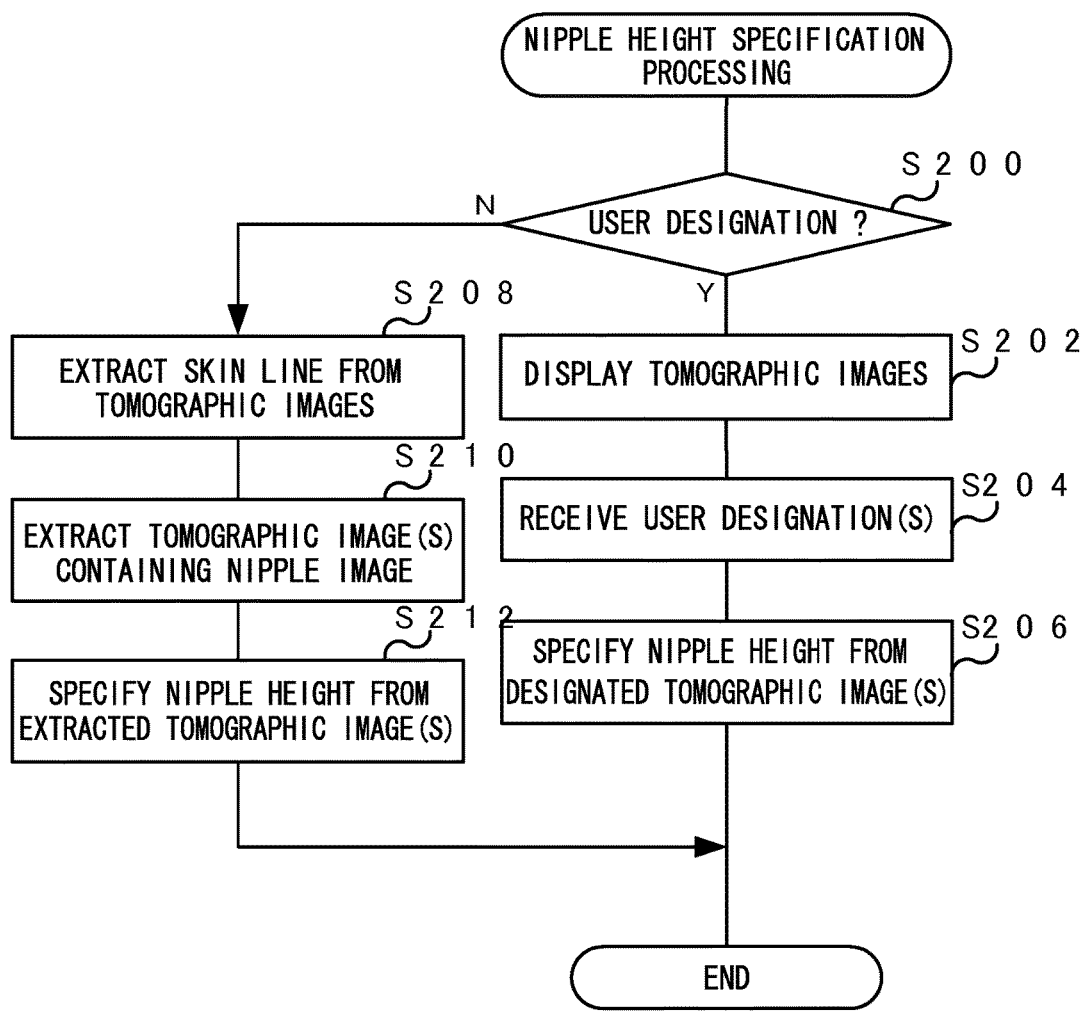
FIG. 7 is a flowchart showing an example of the flow of nipple height specification processing in the image display control processing in accordance with the present exemplary embodiment.

Then, in step S102, specification processing for specifying the nipple height is carried out. FIG. 7 shows a flowchart of an example of the flow of the nipple height specification processing.

In step S200, a determination is made as to whether a designation has been received from the user. In the present exemplary embodiment, the nipple height is specified on the basis of a tomographic image designated by the user or of an extracted tomographic image that includes an image of the nipple. Step S200 determines how the nipple height is to be specified. In a case in which a command by which the user designates a tomographic image is received from the console 16 or the radiation image interpretation device 18, the result of the determination is affirmative and the radiation image processing device 14 proceeds to step S202.

In step S202, the image display control section 84 controls so as to display the plural generated tomographic images at the display of whichever of the console 16 and the radiation image interpretation device 18 the command is received at (i.e., the display 50 or the display 24).

The user selects a tomographic image that contains the nipple image from among the plural displayed tomographic images, and designates that tomographic image at the radiation image processing device 14 from the operation panel 54 or the operation panel 26. In step S204, the radiation image processing device 14 receives the designation of the tomographic image designated by the user via the interface section 67. The user may designate a plural number of the tomographic images.

In step S206, the nipple height is specified from the designated tomographic image(s), after which the present processing ends. A method for specifying the nipple height may be, for example, if only one tomographic image has been designated, specifying the slice height of this tomographic image as the nipple height. Alternatively, if plural tomographic images have been designated, the method may specify the slice height of the tomographic image thereof whose slice position is central as the nipple height, or may specify a value central to the slice heights of these tomographic images as the nipple height. Which of these methods is used may be set beforehand.

On the other hand, if the nipple height is to be specified on the basis of an extracted tomographic image that contains an image of the nipple, the result of the determination in step S200 is negative and the radiation image processing device 14 proceeds to step S208.

In step S208, the nipple height specification section 82 detects a skin line (a boundary line of the breast image) from the tomographic images. Then, in step S210, a tomographic image that contains the nipple image is extracted on the basis of the detected skin line. Specifically, it is sufficient to use a publicly known method. For example, a tomographic image containing the nipple image is extracted by processing that detects inclinations of the skin line or the like.

In step S212, the nipple height is specified from the extracted tomographic image, after which the present processing ends. A method for specifying the nipple height may be, for example, if only one tomographic image is extracted, specifying the slice height of this tomographic image as the nipple height. Alternatively, if plural tomographic images are extracted, the method may specify the slice height of the tomographic image thereof whose slice position is central as the nipple height. As a further example, the method may specify a value central to the slice heights of these tomographic images as the nipple height. In this case, it is not necessary for a tomographic image to have been generated at the slice height corresponding to the central value. As yet another example, the method may compare the tomographic images and specify the slice height of a tomographic image in which the position of the nipple image is furthest from the thoracic wall side as the nipple height. Which of these methods is used may be set beforehand.

When the nipple height has been specified by the nipple height specification processing in step S102, in the succeeding step S104, the image display control section 84 performs control so as to display a tomographic image, the nipple height and the slice height of the tomographic image at the display that the user is using (the display 50 or the display 24).

Figure 8:
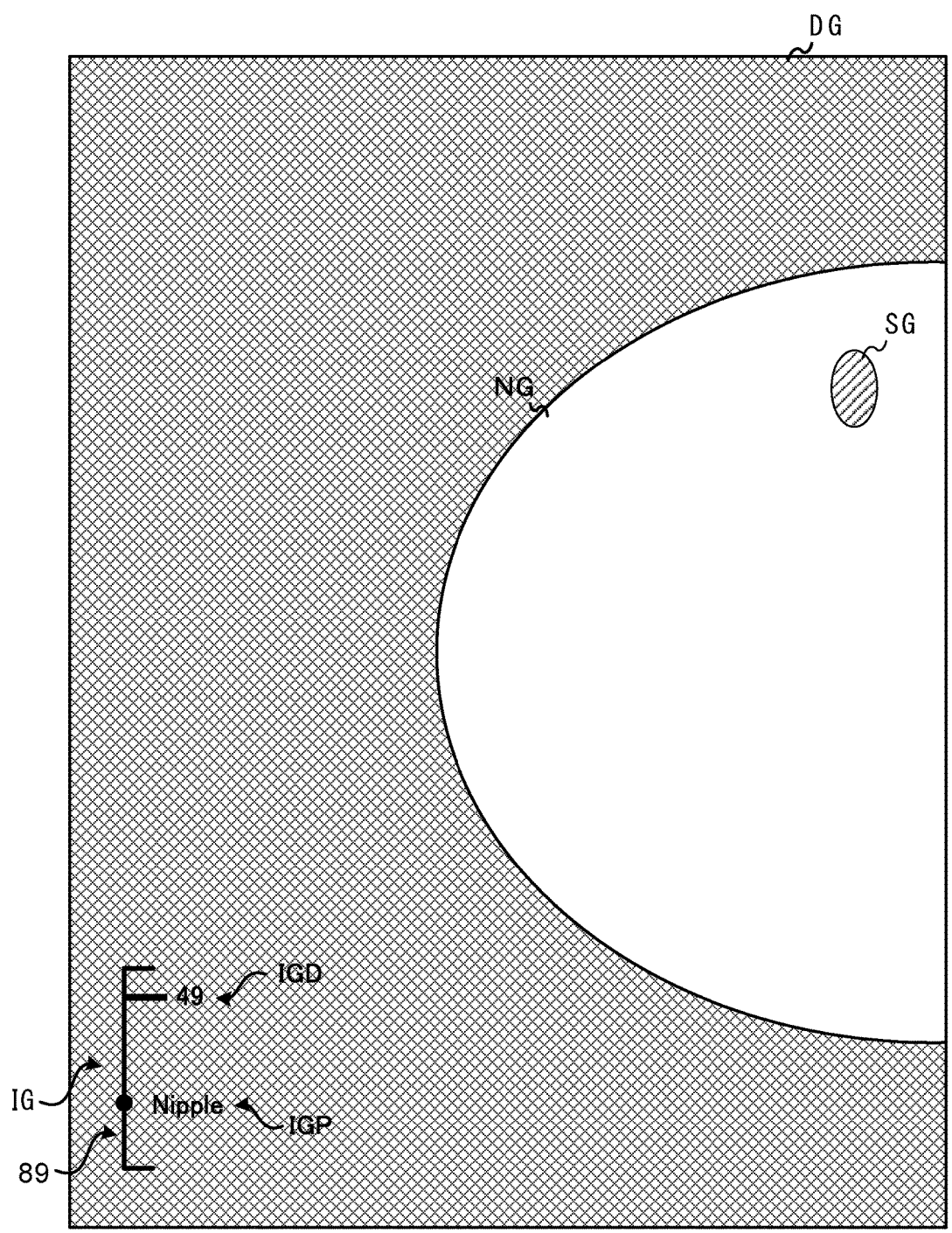
FIG. 8 is a descriptive diagram for describing a tomographic image that contains a breast image and an information image in accordance with the present exemplary embodiment.

Thus, the tomographic image is displayed together with the nipple height and the slice height of the tomographic image at the display 50 or the display 24. FIG. 8 shows a specific example of this display. FIG. 8 shows a tomographic image DG that contains a breast image NG. An information image IG indicating the slice height of the tomographic image DG and the nipple height is displayed on the tomographic image DG, in a region in which the breast image NG is not displayed. In the information image IG shown in FIG. 8, a mark (IGD) indicating the slice height and a mark (IGP) indicating the nipple height (position) are displayed on an axis 89 representing a scale that shows the thickness of the breast N that is compressed by the compression plate 36, with the imaging surface 34 being at the lower side thereof in the drawing. As a specific example, the mark IGD in the information image IG shown in FIG. 8 shows a case in which the slice height is 49 mm.

The user may recognize from the information image IG that the tomographic image DG shown in FIG. 8 is at a position higher than the nipple. In this case in which an object of interest image SG of an object of interest S, such as a tumor, calcinosis or the like, is included in the breast image NG shown in FIG. 8, the user can see that the object of interest S is at the upper side relative to the nipple. Although a nipple image is not included in the tomographic image DG shown in FIG. 8, if it is assumed that the nipple is close to the central region of the breast image NG, it can be understood whether the object of interest S is to the left or right relative to the nipple.

Thus, because the information image IG is displayed together with the tomographic image DG, an approximate position, by reference to the nipple, of the object of interest corresponding to the object of interest image SG included in the tomographic image DG may be perceived.

Then, in step S106, a determination is made as to whether an object of interest S (the object of interest image SG) or a region in the tomographic image DG displayed at the display (the display 50 or the display 24) has been designated. In the present exemplary embodiment, in a case in which an object of interest image SG or region is designated in a tomographic image obtained by one of CC imaging and MLO imaging, how the position of the designated object of interest image SG or region matches the position of the same in the tomographic image obtained by the other kind of imaging is specified. Further, in the present exemplary embodiment control is performed so as to display a mark representing the specified position together with the tomographic image obtained by the other kind of imaging.

Figure 9:
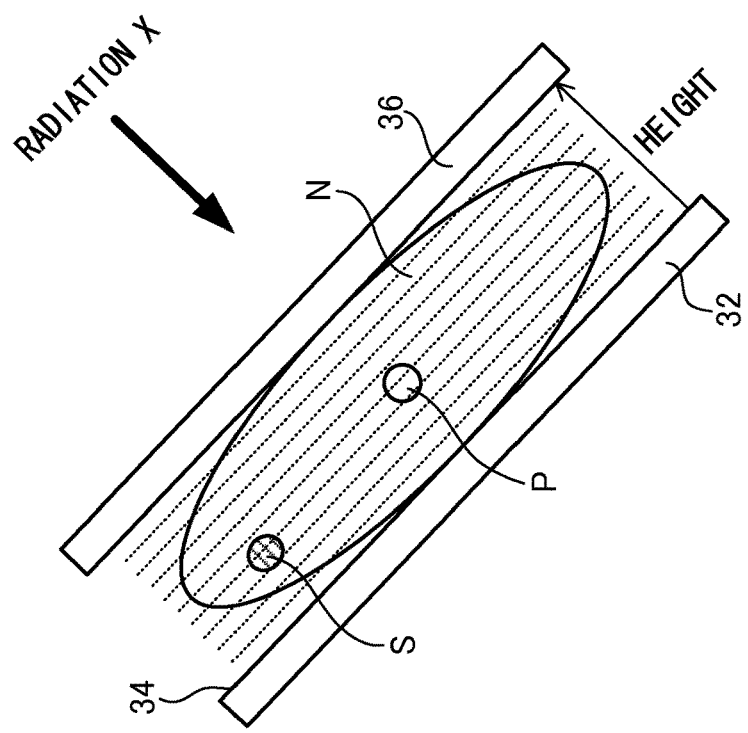
FIG. 9 is a descriptive diagram for describing a state in which a breast is compressed by a compression plate at a time of CC imaging and a state in which the breast is compressed by the compression plate at a time of MLO imaging, in accordance with the present exemplary embodiment.
Figure 9:
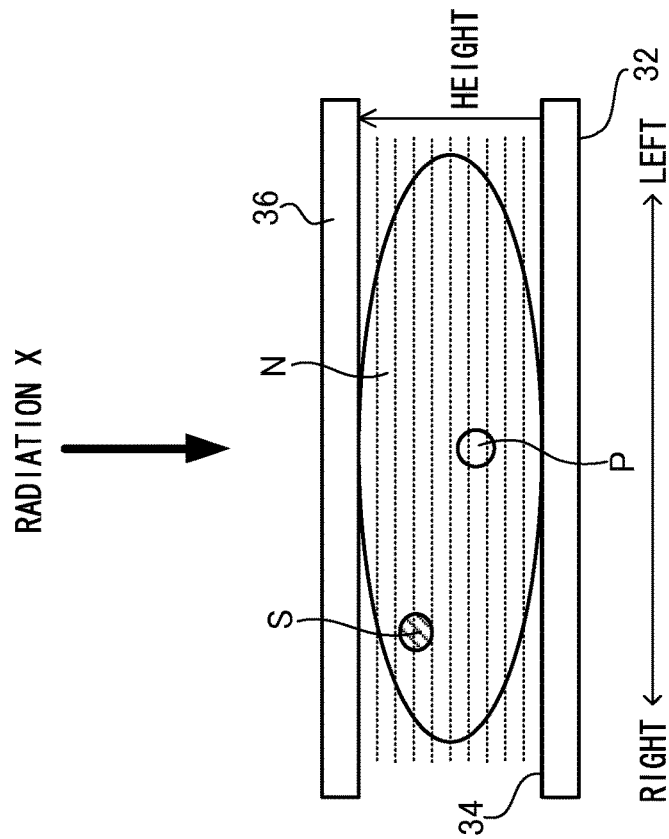

In general, even though an object of interest is the same, it does not appear at the same position and in the same shape in a tomographic image obtained by CC imaging and a tomographic image obtained by MLO imaging. This is specifically described with reference to FIG. 9. FIG. 9 shows a state in which the breast N is compressed by the compression plate 36 at a time of CC imaging, and a state in which the breast N is compressed by the compression plate 36 at a time of MLO imaging. The dotted lines in FIG. 9 show slice planes of the tomographic images. As shown in FIG. 9, the compression states of the breast N differ between CC imaging and MLO imaging. Moreover, the imaging directions differ between CC imaging and MLO imaging. Therefore, when viewed by reference to the imaging surface 34, the position of a nipple P and the position of an object of interest S differ between CC imaging and MLO imaging. Therefore, in a case in which, for example, an image of an object of interest S that has been found in a tomographic image obtained by CC imaging is to be viewed in a tomographic image obtained by MLO imaging, even if a tomographic image at the same slice height as the CC imaging tomographic image in which the object of interest was found is viewed, an image of the object of interest S (an object of interest image SG) may not appear. Moreover, because the position and shape of the object of interest S are different, it may be hard for the user to find the object of interest image SG.

Accordingly, in the present exemplary embodiment, it is made easier for a user to find an object of interest image SG in such a case, by a mark indicating the position of an object of interest that the user has observed being displayed in the tomographic images.

Figure 10:
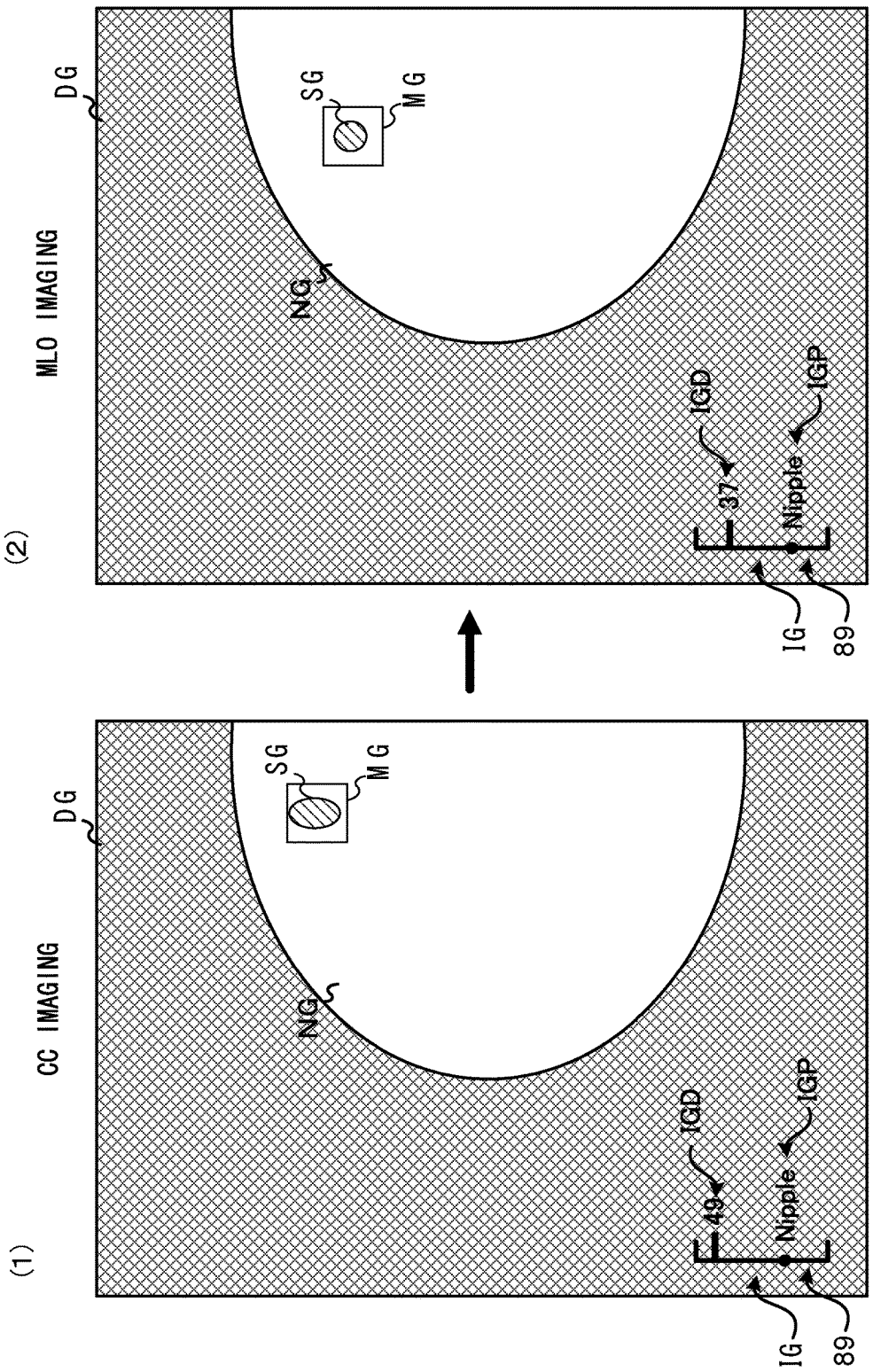
FIG. 10 is a descriptive diagram for describing designation by a user of a region that contains an object of interest image in a tomographic image obtained by CC imaging, and marking of the designated position in accordance with MLO imaging, in accordance with the present exemplary embodiment.

The user interpreting a tomographic image DG designates an object of interest image SG or a region in the tomographic image DG that is being displayed, from the operation panel 54 or the operation panel 26. For example, the user designates the object of interest image SG itself or a region containing the object of interest image SG. In FIG. 10, (1) shows a specific example in which the user has designated a region containing an object of interest image SG. In FIG. 10, (1) shows a state in which the user has designated a region MG that contains the object of interest image SG in a tomographic image DG obtained by CC imaging. Below, a case is described in which, as illustrated by the specific example in FIG. 10, a position is marked in a tomographic image DG obtained by MLO imaging that corresponds to the position of the designated object of interest image SG or region (hereinafter referred to as "the designated position") in the tomographic image DG obtained by CC imaging.

Hence, in the case in which the user has made this designation, the result of the determination in step S106 is affirmative and the radiation image processing device 14 proceeds to step S108. In step S108, the designated position that has been designated is detected by the position detection section 85. In a case in which an object of interest image SG has been designated, the position of the object of interest S corresponding to the object of interest image SG is detected. Alternatively, in a case in which a region has been designated, the position of the region or, using a publicly known image analysis technique or the like, an object of interest image SG in the region is detected. Thus, the position of the object of interest S corresponding to the detected object of interest image SG is detected. Then, in step S110, a designated position corresponding to the designated position detected in step S108 is specified for the other kind of imaging. In the case illustrated in FIG. 10, the location of the designated position in the MLO image is specified. In the information image IG shown in FIG. 10, a mark (IGD) indicating the slice height and a mark (IGP) indicating the nipple height (position) are displayed on an axis 89 representing a scale that shows the thickness of the breast N that is compressed by the compression plate 36.

Herein, the meaning of the "position" that is detected includes a three-dimensional position in the left-and-right direction and the height direction by reference to the imaging surface 34. A method of detection of the position of the object of interest S in a CC image is not restricted, but preferably calculates the position by reference to the position of the nipple P (for example, a distance from the nipple P and the like).

A method of specification of the designated position in the MLO image may be, for example, a method, similar to the method of detection of the position of the object of interest S, that calculates the position by reference to the position of the nipple P. As a further example, the method of specification may be a method of obtaining a table, a computational expression or the like beforehand that represents correspondences between three-dimensional positions in CC images and three-dimensional positions in MLO images, and specifying the position on the basis of these correspondences. Which method is used may be set in advance in accordance with specification accuracy and the like.

When the designated position has been specified in the MLO image, in the succeeding step S112, a tomographic image with a predetermined slice thickness is reconstructed by the tomographic image generation section 80 on the basis of the plural radiation images obtained by MLO imaging. This reconstruction is performed in accordance with a publicly known reconstruction method.

Then, in step S114, the radiation image processing device 14 specifies a tomographic image from the MLO imaging that corresponds to the designated position specified in step S110. In a case in which a tomographic image corresponding to the actual designated position that has been specified has not been generated, the closest position in a tomographic image that has been generated may be specified.

In step S116, similarly to step S102 described above, specification processing is performed to specify the height of the nipple P for the tomographic image from MLO imaging, after which the radiation image processing device 14 proceeds to step S118.

In step S118, the image display control section 84 performs control so as to cause the tomographic image DG obtained by MLO imaging, the height of the nipple P and the slice height of the tomographic image (the information image IG), and a mark MG indicating the designated position to be displayed at the display that the user is using (the display 50 or the display 24). In FIG. 10, (2) shows a specific example of the image that is displayed.

In the present exemplary embodiment, when the tomographic image DG obtained by MLO imaging is being displayed, the tomographic image DG specified in step S114 is initially displayed. Thus, the tomographic image DG containing the object of interest image SG or the like designated by the user is displayed at the display (the display 50 or the display 24) first. This initial display need not be performed, in which case the processing of step S114 described above may be omitted.

Because the position of the object of interest S changes in accordance with the state of the breast N and the manner of compression, there is a concern that the designated position in the one kind of imaging (CC imaging) may not be accurately specified in the other kind of imaging (MLO imaging). However, because the approximate position is known in advance, the user may find the object of interest image SG easily. Considering a case in which the approximate position is specified, the mark MG indicating the designated position may be displayed so as to show a range that contains the designated position that has been specified and is larger than the designated position that has been specified. Alternatively, rather than the mark MG that indicates the designated position being displayed, the image region of the display (the display 50 or the display 24) at which the tomographic image DG is displayed may be divided in advance into a plural number of regions (division regions), and information indicating which of the division regions contains the designated position that has been specified may be displayed.

When the processing of step S118 is complete, the radiation image processing device 14 returns to step S106. In a case in which the result of the determination in step S106 is affirmative, the present processing is repeated. On the other hand, in a case in which the result of the determination is negative, the radiation image processing device 14 proceeds to step S120. In step S120, a determination is made as to whether the present processing is complete. If another tomographic image is to be generated or suchlike and the present processing is not complete, the result of this determination is negative, the radiation image processing device 14 returns to step S100, and the present processing is repeated. On the other hand, if the processing is complete, the result of the determination is affirmative and the present processing ends.

In the present exemplary embodiment as described hereabove, a tomographic image DG is generated by the tomographic image generation section 80, and the height of the nipple P by reference to the imaging surface 34 is specified by the nipple height specification section 82 on the basis of the generated tomographic image DG. The image display control section 84 controls a display at the display (the display 50 or the display 24) via the interface section 67 such that the generated tomographic image DG is displayed together with the information image IG, showing the height of the nipple P and the slice height of the tomographic image DG that is being displayed.

Because this information image IG is displayed together with the tomographic image DG, the user who has found the object of interest image SG of the object of interest S may perceive the position of the object of interest S relative to the nipple P.

Therefore, if the compression state of the breast N changes, the position of the object of interest S may be easily perceived even, for example, in an uncompressed state or a case in which the imaging method is changed.

In the present exemplary embodiment, the mark IGD showing the slice height of the tomographic image DG is displayed in the information image IG. However, the mark IGD need not be displayed. In the present exemplary embodiment, because at least the mark IGP showing the height of the nipple P is displayed, a user may recognize the height of the nipple P and easily perceive the three-dimensional position of the object of interest S by reference to the nipple P.

Furthermore, the information image IG, the mark IGD showing the slice height, and the mark IGP showing the height of the nipple P are not particularly limited. However, these display positions are preferable for regions in which the nipple image NG is not displayed.

In the present exemplary embodiment, a case is described in which CC imaging and MLO imaging are carried out, but this is not limiting. For example, instead of MLO imaging, medio-lateral (ML) imaging (imaging in a side view direction) may be carried out. Further yet, ML imaging may be carried out in addition to CC imaging and MLO imaging.

The way in which the information image IG is displayed is not limited by the present exemplary embodiment (see FIG. 8). It is sufficient to display the slice height of the tomographic image DG that is being displayed and the height of the nipple P. In FIG. 8, the height of the nipple P is shown by a point (a circle). However the nipple P generally has some thickness. In consideration of this thickness, the height (position) of the nipple P may be shown by the display of a range of the slice heights of all tomographic images DG in which the nipple image is detected.

In the present exemplary embodiment, the height of the nipple P is specified using the tomographic images DG, but this is not limiting. For example, a further two-dimensional image may be generated on the basis of the generated tomographic images DG, and the height of the nipple P may be specified using this generated two-dimensional image. The height of the nipple P may also be specified using the radiation images that are acquired from the electronic cassette 20 for the generation of the tomographic images DG.

The height of the nipple P that has been specified may be memorized in association with the generated tomographic images DG, the radiation images acquired from the electronic cassette 20 or the like. In a case in which the height of the nipple P has been memorized in association with the tomographic images DG or radiation images in this manner, the memorized height of the nipple P may be acquired instead of the specification processing for the height of the nipple P that is described above being carried out.

In the present exemplary embodiment, a case is described in which, in the specification processing that specifies the height of the nipple P, the generated tomographic images DG are displayed and the user designates a tomographic image DG among those images. However, the process by which the user designates the tomographic image DG is not limited. For example, the height of the nipple P may be specified by a pseudo-three-dimensional image being displayed and the user designating a point in this image. The local slice position (height) of the point may be acquired and the height of this slice specified to be the height of the nipple P.

The radiation that is used for the capture of the radiation images is not particularly limited; X-rays, gamma rays and the like may be employed.

In other respects, the structures and operations of the radiation imaging system 1, radiation imaging device 10 and radiation image processing device 14 described in the present exemplary embodiment are examples and it will be clear that these may be modified in accordance with conditions within a scope not departing from the spirit of the present disclosure. Moreover, the flow of the capture of radiation images and the flow of the image display control processing described in the present exemplary embodiment are examples and it will be clear that these may be modified in accordance with conditions within a scope not departing from the spirit of the present disclosure.

In a case in which an image of an object of interest such as a tumor, a calcinosis or the like is found in a tomographic image, even if the position of that tomographic image can be identified, for example, by the identity of the slice in JP-A No. 2010-94397, it may be difficult to perceive the position of the object of interest that has been found, particularly the three-dimensional position thereof.

In mammography in particular, the breast is generally imaged in a compressed state. Therefore, it may be difficult to perceive the position of an object of interest if there is a change in the state of compression, for example, to a non-compressed state.

An object of the present disclosure is to provide an image display system, a radiation imaging system, an image display control program and an image display control method that make it easier to perceive the position of an object of interest.

A first aspect of the present disclosure is an image display system including: a tomographic image generation unit that irradiates radiation, from a radiation irradiation unit disposed to oppose a radiation image detector, at a breast on the radiation image detector from different angles, acquires a plurality of radiation images captured by the radiation image detector at the respective angles from the radiation image detector and, on the basis of the acquired plurality of radiation images, generates a tomographic image that is reconstructed by reference to a detection plane of the radiation image detector; a height specification unit that specifies a height of a nipple of the breast by reference to the detection plane; and a display control unit that controls to cause a display unit to display the tomographic image together with information relating to the nipple height specified by the height specification unit.

In a second aspect of the present disclosure, in the first aspect described above, it is preferable if the tomographic image generation unit generates a first tomographic image on the basis of a plurality of radiation images acquired by a first imaging and generates a second tomographic image on the basis of a plurality of radiation images acquired by a second imaging, in which an angle of the detection plane relative to the breast is different from the first imaging, the image display system further includes a position specification unit that specifies a corresponding position in the second tomographic image of at least one of an object of interest or region designated in the first tomographic image, the first tomographic image being displayed at the display unit, and the display control unit controls to display the second tomographic image together with information representing the corresponding position specified by the position specification unit.

In a third aspect of the present disclosure, in the second aspect described above, the position specification unit may specify the position in the second tomographic image of the at least one of an object of interest or region designated in the first tomographic image by reference to a position of the nipple.

In a fourth aspect of the present disclosure, in the second aspect described above, the position specification unit may specify the position in the second tomographic image of the at least one of an object of interest or region designated in the first tomographic image on the basis of pre-specified correspondences between positions in the first tomographic image and positions in the second tomographic image.

In a fifth aspect of the present disclosure, in the aspects described above, the height specification unit may specify the height of the nipple by reference to the detection plane on the basis of a tomographic image, extracted from a plurality of the tomographic images generated by the tomographic image generation unit, that contains an image of the nipple.

In a sixth aspect of the present disclosure, the aspects described above may further include a receiving unit that receives a designation of a tomographic image that contains an image of the nipple, wherein the height specification unit specifies the height of the nipple by reference to the detection plane on the basis of the tomographic image received by the reception unit.

In a seventh aspect of the present disclosure, in the aspects described above, the display control unit may cause the display unit to display information relating to a height of the tomographic image being displayed at the display unit by reference to the detection plane.

An eighth aspect of the present disclosure is a radiation imaging system including: a radiation imaging device that detects radiation irradiated from a radiation irradiation unit with a radiation image detector and captures a radiation image; an image display system according to the aspects of the present disclosure described above, the image display system acquiring the radiation image captured by the radiation imaging device; and a display unit that is controlled by the image display system.

A ninth aspect of the present disclosure is an image display control program that causes a computer to function as: a tomographic image generation unit that irradiates radiation, from a radiation irradiation unit disposed to oppose a radiation image detector, at a breast on the radiation image detector from different angles, acquires a plurality of radiation images captured by the radiation image detector at the respective angles from the radiation image detector and, on the basis of the acquired plurality of radiation images, generates a tomographic image that is reconstructed by reference to a detection plane of the radiation image detector; a height specification unit that specifies a height of a nipple of the breast by reference to the detection plane; and a display control unit that controls to cause a display unit to display the tomographic image together with information relating to the nipple height specified by the height specification unit.

A tenth aspect of the present disclosure is an image display control method including: a tomographic image generation step of irradiating radiation, from a radiation irradiation unit disposed to oppose a radiation image detector, at a breast on the radiation image detector from different angles, acquiring a plurality of radiation images captured by the radiation image detector at the respective angles from the radiation image detector by irradiating radiation, from the radiation irradiation unit disposed to oppose the radiation image detector, at the breast on the radiation image detector from different angles and plurally capturing at the respective angles from the radiation image detector and, on the basis of the acquired plurality of radiation images, generating a tomographic image that is reconstructed by reference to a detection plane of the radiation image detector; a height specification step of specifying a height of a nipple of the breast by reference to the detection plane; and a display control step of controlling to cause a display unit to display the tomographic image together with information relating to the nipple height specified by the height specification step.

According to the present disclosure, an effect is provided in that the position of an object of interest is easier to perceive.

The disclosures of Japanese Patent Application No. 2012-218256 are incorporated into the present specification by reference in their entirety.

All references, patent applications and technical specifications cited in the present specification are incorporated by reference into the present specification to the same extent as if the individual references, patent applications and technical specifications were specifically and individually recited as being incorporated by reference.

What is claimed is:

1. An image display system comprising:
    a tomographic image generation unit that:
        comprises an x-ray source disposed opposite an x-ray image detector with an examined breast of a subject there between, such that the breast is irradiated by x-rays from the source, said x-rays incident upon the breast at different angles of incidence with respect to the x-ray image detector,
        acquires a plurality of x-ray images captured by the x-ray image detector at the respective angles from the x-ray image detector, and
        generates a tomographic image on the basis of the acquired plurality of x-ray images, wherein said tomographic image is reconstructed with respect to a detection plane of the x-ray image detector;
    a height specification unit that specifies a height of a nipple of the breast with respect to the detection plane; and
    a display control unit that causes a display unit to display the tomographic image together with information relating to the nipple height specified by the height specification unit; wherein
    the display unit, on a graphical axis on the screen of the display that shows the thickness of the breast, (1) displays information that indicates the height of a slice of the tomographic image that is displayed, and (2) displays information that indicates a location of the nipple height, the location of the nipple height being relative to the thickness of the breast shown on the axis; and wherein
    the axis that shows thickness of the breast is graphically displayed in the tomographic image that is displayed, the axis is graphically displayed in a specific area in the displayed tomographic image, in the specific area, the breast is not displayed, and the information that indicates the nipple height is displayed with respect to the axis, and the information that indicates the nipple height is graphically displayed in the specific area.

2. The image display system according to claim 1, wherein:
    the tomographic image generation unit generates a first tomographic image on the basis of a plurality of x-ray images acquired by a first imaging session and generates a second tomographic image on the basis of a plurality of x-ray images acquired by a second imaging session, in which an angle of the detection plane relative to the breast is different from the first imaging session, the image display system further includes a position specification unit, wherein said position specification unit specifies, in the second tomographic image, a position that corresponds to at least one of an object of interest or a region designated in the first tomographic image, and the display control unit further causes the display unit to display the second tomographic image together with information representing the corresponding position specified by the position specification unit.

3. The image display system according to claim 2, wherein the position specification unit specifies the position, in the second tomographic image, of the at least one of an object of interest or a region designated in the first tomographic image, by reference to a position of the nipple.

4. The image display system according to claim 2, wherein the position specification unit specifies the position, in the second tomographic image, of the at least one of an object of interest or a region designated in the first tomographic image, on the basis of pre-specified correspondences between the position in the first tomographic image and the position in the second tomographic image.

5. The image display system according to claim 1, wherein the height specification unit specifies the height of the nipple by reference to the detection plane, on the basis of a tomographic image extracted from a plurality of the tomographic images generated by the tomographic image generation unit, wherein said extracted tomographic image contains an image of the nipple.

6. The image display system according to claim 1, further comprising a receiving unit that receives a designation of a tomographic image that contains an image of the nipple, wherein the height specification unit specifies the height of the nipple by reference to the detection plane on the basis of the designation of the tomographic image received by the receiving unit.

7. The image display system according to claim 1, wherein the display control unit causes the display unit to display information relating to a height of the tomographic image by reference to the detection plane.

8. A radiation imaging system comprising:

an x-ray imaging device that detects x-rays irradiated from an x-ray irradiation unit with an x-ray image detector and captures an x-ray image;

the image display system according to of claim 1, the image display system acquiring the x-ray image captured by the x-ray imaging device; and a display unit that is controlled by the image display system.

9. A non-transitory recording medium storing an image display control program causing a computer to execute a process, the process comprising:

providing an x-ray source disposed opposite an x-ray image detector with an examined breast of a subject there between, such that the breast is irradiated by x-rays from the source, said x-rays incident upon the breast at different angles of incidence with respect to the x-ray image detector;

acquiring a plurality of x-ray images captured by the x-ray image detector at the respective angles from the radiation image detector;

generating a tomographic image on the basis of the acquired plurality of x-ray images, wherein said tomographic image is reconstructed with respect to a detection plane of the x-ray image detector;

specifying a height of a nipple of the breast with respect to the detection plane; and controlling a display unit so as to display the tomographic image together with information relating to the specified nipple height; wherein the display unit, on a graphical axis on the screen of the display that shows thickness of the breast, (1) displays information that indicates the height of a slice of the tomographic image that is displayed, and (2) displays information that indicates a location of the nipple height, the location of the nipple height being relative to the thickness of the breast shown on the axis; and wherein the axis that shows thickness of the breast is graphically displayed in the tomographic image that is displayed, the axis is graphically displayed in a specific area in the displayed tomographic image, in the specific area, the breast is not displayed, and the information that indicates the nipple height is displayed with respect to the axis, and the information that indicates the nipple height is graphically displayed in the specific area.

10. An image display control method comprising:

providing a tomographic image generation unit that comprises an x-ray source disposed opposite an x-ray image detector with an examined breast of a subject there between, such that the breast is irradiated by x-rays from the source, said x-rays incident upon the breast at different angles of incidence with respect to the x-ray image detector, acquiring a plurality of x-ray images captured by the x-ray image detector;

generating a tomographic image on the basis of the acquired plurality of x-ray images, wherein said tomographic image is reconstructed with respect to a detection plane of the x-ray image detector;

specifying a height of a nipple of the breast with respect to the detection plane; and controlling a display unit so as to display the tomographic image together with information relating to the specified nipple height; wherein the display unit, on a graphical axis on the screen of the display that shows thickness of the breast, (1) displays information that indicates the height of a slice of the tomographic image that is displayed, and (2) displays information that indicates a location of the nipple height the location of the nipple height being relative to the thickness of the breast shown on the axis; and wherein the axis that shows thickness of the breast is graphically displayed in the tomographic image that is displayed, the axis is graphically displayed in a specific area in the displayed tomographic image, in the specific area, the breast is not displayed, and the information that indicates the nipple height is displayed with respect to the axis, and the information that indicates the nipple height is graphically displayed in the specific area.

11. The image display system according to claim 1, wherein in a case in which a plurality of tomographic images that include a nipple are specified, the nipple height is a central value of the slice positions of the specified plurality of tomographic images.

12. The image display system according to claim 1, wherein the information that indicates the nipple height is displayed on the axis.

* * * * *